United States Patent [19]
Von Werner

[11] Patent Number: 5,557,020
[45] Date of Patent: Sep. 17, 1996

[54] HIGH-PURITY PERFLUORO-4-METHYL-2-PENTENE AND ITS PREPARATION AND USE

[75] Inventor: Konrad Von Werner, Garching, Germany

[73] Assignee: Hoechst Aktiengesellschaft, Germany

[21] Appl. No.: 321,982

[22] Filed: Oct. 12, 1994

Related U.S. Application Data

[62] Division of Ser. No. 166,140, Dec. 10, 1993, abandoned.

[30] Foreign Application Priority Data

Dec. 12, 1992 [DE] Germany .................. 42 41 969.7

[51] Int. Cl.⁶ .................................................. C07C 17/38
[52] U.S. Cl. .................................................. 570/177
[58] Field of Search ................................. 570/177

[56] References Cited

U.S. PATENT DOCUMENTS

| | | |
|---|---|---|
| 2,918,501 | 12/1959 | Brehm et al. . |
| 3,321,383 | 5/1967 | Scherer et al. . |
| 3,917,724 | 11/1975 | Martini . |
| 4,042,638 | 8/1977 | Ozawa et al. . |
| 4,766,261 | 8/1988 | Bierl .......................... 570/177 |
| 4,973,774 | 11/1990 | Rozen et al. . |
| 5,254,774 | 10/1993 | Prokop . |
| 5,352,785 | 10/1994 | Herzberg .................. 570/177 |

FOREIGN PATENT DOCUMENTS

| | | |
|---|---|---|
| 668929 | 8/1963 | Canada . |
| 2068128 | 11/1992 | Canada . |
| 0367256 | 5/1990 | European Pat. Off. . |
| 0512502 | 11/1992 | European Pat. Off. . |
| 615057 | 7/1978 | U.S.S.R. . |

OTHER PUBLICATIONS

Chemical Abstracts, vol. 83, No. 19, Nov. 10, 1975, Columbus Ohio (abstract No. 163550).
Chemische Berichte, Bd. 106, Nr. 9, 1973 pp. 2850–2959, Sigmar P. V. Halasz et al.

*Primary Examiner*—Alan Siegel
*Attorney, Agent, or Firm*—Connolly & Hutz

[57] ABSTRACT

The toxic perfluoro-2-methyl-2-pentene can be removed from perfluoro-4-methyl-2-pentene by treating the mixture with lower alkanols, the toxic isomer being converted into high boiling-point compounds which can be easily removed. The high-purity perfluoro-4-methyl-2-pentene so obtained is suitable as a substitute for chlorofluorocarbons.

7 Claims, No Drawings

HIGH-PURITY PERFLUORO-4-METHYL-2-PENTENE AND ITS PREPARATION AND USE

This application is a divisional of Ser. No. 08/166,140 filed Dec. 10, 1993 now abandoned.

DESCRIPTION

The invention relates to a perfluoro-4-methyl-2-pentene, referred to hereinafter as (I), having a content of perfluoro-2-methyl-2-pentene, referred to hereinafter as (II), of below 1000 ppm, preferably below 100 ppm and particularly below 10 ppm. The invention further relates to the preparation of such a high-purity (I) by removal of (II) from the corresponding starting materials. The invention further relates to the use of high-purity (I) as a substitute for chlorofluorocarbons.

(I), in particular the trans-isomer, is the main product in the dimerization of hexafluoropropene. However, in all known dimerization processes for hexafluoropropene some proportion of (II) is formed, this being toxic by inhalation.

A process for preparing dimers of hexafluoropropene with a high proportion of (I) and a low content of (II) has already been proposed, wherein the dimerization of the hexafluoropropene is carried out in an aprotic solvent in the presence of an adduct of an amine which contains no NH groups and a metal fluoride (U.S. patent application Ser. No. 08/111,643, filed Aug. 25, 1993). This process yields dimerization products in which the content of (II) has been reduced to as little as 0.2%.

It has now been found that the content of (II) in mixtures comprising mostly (I) can be reduced to a content of below 1000 ppm of (II) by treating the mixtures with lower alkanols and catalytic amounts of a base. In this way (II) is converted into high boiling-point compounds which can readily be separated from (I) by distillation.

Preferred embodiments of the present invention will now be more particularly described.

Suitable bases are essentially alkali metal hydroxides such as NaOH or KOH if mild conditions, i.e. in particular low temperatures, are used, since otherwise the selectivity of the reaction is reduced. Alkali metal and ammonium carbonates and hydrogen carbonates such as sodium carbonate, potassium or tetramethylammonium hydrogen carbonate are suitable. Furthermore, metal fluorides, in particular alkali metal fluorides such as KF can be used, although it should be noted that in that case fluoride ions will pass into the wash water. Particular preference is given to tertiary amines, which are effective even in very small amounts and which ensure a high selectivity, such as lower trialkylamines or peralkylated chelating diamines or triamines, which may also contain ether-oxygen in the alkyl or alkylene groups. Such amines were proposed for the process of U.S. patent application Ser. No. 08/111,643. Preference is given to from 0.05 to 0.1 mol of amine per mole of (II).

Preferred starting materials are products of the process proposed in U.S. patent application Ser. No. 08/111,643. These products contain on the one hand only small amounts of (II) and on the other hand, as crude products, already suitable amines (with or without fluorides) as catalysts suitable for the process of the invention.

However, other starting materials having a predominant content of (I) besides (II) can also be used, such as those obtainable, for example, according to U.S. Pat. No. 2,918,501 by oligomerization of hexafluoropropene, with halides and solvents selected from the group comprising alkyl-substituted amides, phenylamines and sulfoxides. In further known processes for the dimerization and trimerization of hexafluoropropene, catalysts used are tris[2-(2H-hexafluoropropoxy)ethyl]amine in acetonitrile [Halasz et al., Chem. Ber. 106 (1973) 2950 to 2955] or complex salts of an alkali metal halide with a crown ether (U.S. Pat. No. 4,042,638).

Suitable lower alkanols are all compounds which can form high boiling-point compounds with (II). It is advantageous to select easily removable alkanols, ie. for example readily water-soluble compounds. Suitable alkanols have from 1 to 6 carbon atoms and alkyl radicals which may be linear, branched or cyclic. Preference is given to alkanols having from 1 to 3 carbon atoms, particularly methanol, since this reacts particularly rapidly and selectively.

The alkanol is preferably used in a stoichiometric excess, based on the content of (II). Some excess is advantageous since the main part of the alkanol separates out as an upper phase after the reaction and can therefore be readily removed and recycled to the process. The amount selected in practice is about 5 to 15% by volume of alkanol, based on the volume of the (I) to be purified or of the oligomerization product of hexafluoropropene.

The treatment of the starting material with the alkanol is carried out in the liquid phase, usefully at temperatures from about −20° C. to about 40° C., advantageously at from 0° C. to about 35° C., preferably at from 15° C. to 30° C., particularly at from 20° C. to 25° C. Since the starting material forms a two-phase mixture with the lower alkanol good contact between the alkanol and (II) must be provided. Vigorous stirring or shaking in customary equipment shortens the reaction time.

The conversion can be monitored using customary analytical procedures, for example by gas chromatography. The treatment time is of course dependent on the desired reduction in the content of (II), on the reactivity of the alkanol and on the effectiveness of the catalyst. Usually times of up to 6 hours, mostly up to 3 hours, are sufficient to reduce the content of (II) to below 10 ppm.

At the end of the treatment the reaction mixture is allowed to separate into two phases and the alcohol phase is removed. This can be used without further purification for a new batch.

The (I)-containing phase is separated by distillation from the high boiling-point products formed from (II). (I) can thus be obtained with a content of (II) below the analytical detection level.

The high-purity (I) obtainable according to the invention is usually a cis-trans mixture having a trans content of about 95%. It can also contain proportions of trimers of hexafluoropropene, which usually do not interfere with the use as substitutes for chlorofluorocarbons.

The (I) obtainable according to the invention is particularly suitable for use as a heat transfer, cooling and insulation medium, especially for two-phase evaporative cooling of electrical and electronic components, for example as cooling medium for the two-phase evaporative cooling of gases or liquids without high-voltage insulation, preferably in a heat exchanger tube, or as a heat transfer medium where the heat energy passes by single-phase convection from the gaseous, liquid or solid material to be cooled to another gaseous, liquid or solid material to be heated (U.S. patent application Ser. No. 08/132,742 of Oct. 6, 1993).

The examples below illustrate the invention.

EXAMPLE 1

Preparation of dimers of hexafluoropropene (HFP):

These experiments were carried out in a 16 l vessel made of electropolished stainless steel and equipped with a controllable agitator, a calibrated inlet for gaseous hexafluoropropene and metering-in facilities for liquids and solids. Heating and cooling of the vessel can be controlled to an accuracy of ±1° C. by means of a circuit with an external plate heat exchanger.

A catalyst solution is first prepared in the laboratory from the components below:

- 1.5 l of acetonitrile (dried by distillation over a little calcium hydride and storage over 3 Å molecular sieve),
- 69.7 g (0.6 mol) of N,N,N',N'-tetramethylethylenediamine (dried over 4 Å molecular sieve),
- 34.9 g (0.6 mol) of potassium fluoride powder (dried by stirring the powder at 180° C./0.5 mbar).

The components are added in this order under dry nitrogen with the agitator running and are vigorously stirred at from 30° to 40° C. for 1 hour. This results in a yellowish solution which scarcely contains any solid potassium fluoride.

This solution is then introduced into the carefully $N_2$-purged 16 l vessel. With the top valve closed the vessel is heated to 40° C. and 16 kg of gaseous HFP is then metered in over a period of 6 hours with the agitator running. The reaction is slightly exothermic. The internal temperature is maintained at from 40° to 50° C. by cooling. The mixture is allowed to react further for another 2 hours at 40° C. and is then cooled, with the agitator turned off, to 15° C.

Through the bottom valve of the vessel 14 kg of crude product are slowly drained into a container which for pressure equalization is connected by the HFP feed line to the vessel (breather line). 2 kg of the product remain with the lighter catalyst phase in the vessel.

The crude product is analyzed by gas chromatography. For the analysis a packed column (5% of GEXE 60 on ®PORASIL C) with a heat-conductivity detector is used (carrier gas: helium). Assignment of the components was determined beforehand by comparison of the retention times and area factors with essentially pure reference compounds. The distribution below is obtained for the fluorine-containing products:

| | |
|---|---|
| $CF_3$—CF=$CF_2$ | 0.2% |
| $(CF_3)_2$CFH | 0.1% |
| trans-$(CF_3)_2$CF—CF=CF—$CF_3$ (I) | 90.1% |
| cis-$(CF_3)_2$CF—CF=CF—$CF_3$ (I) | 5.0% |
| $(CF_3)_2$C=CF—$CF_2CF_3$ (II) | 0.4% |
| Σ HFP trimers | 4.2% |

$^{19}$F-NMR analysis of the crude product at 282.4 MHz (solution in $CDCl_3$/R113, standard: $CF_3CO_2H$) confirmed that the ratio of trans- and cis-dimers of (I) determined by GC corresponds to the molar ratio of these two compounds. This was determined by evaluating the integrals of the fluorine atoms bonded to the double bond. The $^{19}$F-NMR data for the two isomers are shown below (standard: trifluoroacetic acid).

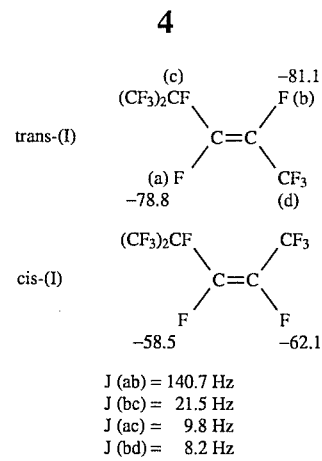

J (ab) = 140.7 Hz
J (bc) =  21.5 Hz
J (ac) =   9.8 Hz
J (bd) =   8.2 Hz

Two further batches were processed with the catalyst solution remaining in the vessel, 14 kg of HFP being reacted each time. After the third charge in all the catalyst solution was separated off from the product. GC analysis gave the product distributions below:

| | Batch 2 | Batch 3 |
|---|---|---|
| $CF_3CF$=$CF_2$ | 0.5% | 1.0% |
| $(CF_3)_2CFH$ | 0.1% | 0.2% |
| trans-$(CF_3)_2$CF—CF=CF—$CF_3$ (I) | 90.1% | 90.3% |
| cis-$(CF_3)_2$CF—CF=CF—$CF_3$ (I) | 5.1% | 5.0% |
| $(CF_3)_2$C=CF—$CF_2CF_3$ (II) | 0.4% | 0.2% |
| $(CF_3)_2$CH—$CF_2CF_2CF_3$ | 0.1% | 0.1% |
| Σ HFP trimers | 3.7% | 3.2% |

The highly toxic perfluoro-2-methyl-1-pentene could not be detected in any of the batches.

A total of 43.5 kg was obtained by combining the crude products. This material still contains traces of impurities derived from the catalyst solution (inter alia ca. 0.03% of tetramethylethylenediamine).

Purification according to the invention:

The abovedescribed crude product was stirred vigorously with 3 l of methanol for 2 hours at ca. 20° C. The phases were subsequently separated. The product phase was purified by counter-current scrubbing in a vertical bubble column filled with Raschig rings. The column was filled with 10 l of water. The fluorinated product was metered in at the top and trickled down the column. At the same time a counter-current of 20 l of water was introduced at the bottom end. The purified product collects at the bottom end of the column in a receiver. After removal of the supernatant water layer the product (43 kg) contained less than 0.005% of water.

For final purification the scrubbed product was distilled at atmospheric pressure via a packed column whose condenser and receiver were cooled to 0° C. by means of a refrigeration unit. A main fraction of 40 kg having a boiling range of from 45.5° to 49.0° C. was obtained.

| Composition by GC: | |
|---|---|
| trans-(I) | 94.7% |
| cis-(I) | 5.3% |

The content of (II) is below 10 ppm. This is the detection limit for (II) in optimized GC analysis. The mass yield is 90% based on hexafluoropropene used.

EXAMPLE 2

300 ml (482 g) of a mixture having the composition below were used:

| | |
|---|---|
| trans-(I) | 89.8% |
| cis-(I) | 4.9% |
| (II) | 5.2% |
| HFP trimers | 0.1% |

This mixture was vigorously stirred with 30 ml of absolute ethanol and 1.69 g of triethylamine [corresponding to 10 mol-% based on (II)] for 4 hours at about 23° C. The mixture was then extracted three times with 0.5 l of ice-water each time. The organic phase was dried with a little sodium sulfate and then distilled at atmospheric pressure via a column whose receiver was cooled to 0° C. A main fraction of 426 g having a boiling range of from 46° to 49° C. was obtained. The composition below was determined by GC and $^{19}$F-NMR:

| | |
|---|---|
| trans-(I) | 94.8% |
| cis-(I) | 5.2% |
| (II) | 320 ppm |

The distillation residue was fractionated via a split-tube column. A first fraction of 6.2 g having a boiling point of from 59° to 61° C. was obtained, which was identified as $(CF_3)_2CH\text{-}CF_2CF_2CF_3$. The main fraction (24.3 g) distilling over at from 107° to 110° C. contained, on the basis of $^{19}$F-NMR and $^1$H-NMR, the two ethers below in a molar ratio of 2.1:1.

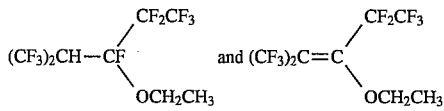

EXAMPLE 3

The reaction and workup were carried out as in Example 2, but using methanol in place of ethanol. GC of a sample taken after 2 hours showed that already at this point in time the content of (II) is less than 0.1%. After 4 hours reaction time, workup gave the fractions below:

439 g of main fraction (bp. 46 to 48.5° C.), comprising:

| | |
|---|---|
| trans-(I) | 94.9% |
| cis-(I) | 5.1% |
| (II) | 118 ppm |

2.8 g of $(CF_3)_2CH\text{—}CF_2CF_2CF_3$ (bp. 59 to 62° C.)
13.5 g (bp. 95 to 98° C.) of a mixture of

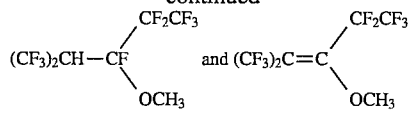

The two ethers are present in a molar ratio of 3.7:1.

What is claimed is:

1. A process for preparing a perfluoro-4-methyl-2-pentene having a content of perfluoro-2-methyl-2-pentene of below 1000 ppm, which comprises:

treating a starting material comprising a major amount of perfluoro-4-methyl-2-pentene and a minor amount of perfluoro-2-methyl-2-pentene, said minor amount being greater than 1000 ppm, with a lower alkanol and a catalytic amount of a base, and removing any compound or compounds, higher boiling than perfluoro-2-methyl-2-pentene, formed from said perfluoro-2-methyl-2-pentene as a result of said treatment.

2. The process as claimed in claim 1, wherein the amount of lower alcohol is stoichiometrically in excess with respect to said minor amount of perfluoro-2-methyl-2-pentene.

3. The process as claimed in claim 1, wherein the said lower alkanol has from 1 to 3 carbon atoms.

4. The process as claimed in claim 1, wherein the treatment with the lower alkanol is carried out at a temperature of from 0° to 35° C.

5. The process as claimed in claim 1, wherein the base is a tertiary amine.

6. The process as claimed in claim 1, wherein the treatment is carried out over a period of up to 3 hours.

7. The process as claimed in claim 1, comprising:

mixing said starting material with said lower alkanol in the presence of said base, thereby forming a mixture having a plurality of liquid phases, providing intimate contact between said liquid phases until the perfluoro-2-methyl-2-pentene is substantially converted into a compound having a higher boiling point than perfluoro-2-methyl-2-pentene, and separating the perfluoro-4-methyl-2-pentene from said lower alkanol and a said compound having a higher boiling point, thereby recovering perfluoro-4-methyl-2-pentene having a content of less than 1000 ppm of perfluoro-2-methyl-2-pentene.

* * * * *